(12) United States Patent
Cary

(10) Patent No.: US 6,197,827 B1
(45) Date of Patent: Mar. 6, 2001

(54) NICOTINE ADDICTION TREATMENT

(75) Inventor: Douglas D. Cary, Great Falls, VA (US)

(73) Assignee: Cary Medical Corporation, Bethesda, MD (US)

( * ) Notice: Subject to any disclaimer, the term of this patent is extended or adjusted under 35 U.S.C. 154(b) by 0 days.

(21) Appl. No.: 09/423,897

(22) PCT Filed: Oct. 2, 1998

(86) PCT No.: PCT/US98/20894

§ 371 Date: Nov. 16, 1999

§ 102(e) Date: Nov. 16, 1999

(87) PCT Pub. No.: WO99/17803

PCT Pub. Date: Apr. 15, 1999

Related U.S. Application Data
(60) Provisional application No. 60/060,794, filed on Oct. 3, 1997.

(51) Int. Cl.[7] .................................................... A61K 31/00

(52) U.S. Cl. .......................... 514/646; 514/649; 514/660; 514/661; 514/811; 514/812; 514/813

(58) Field of Search ................................... 514/646, 649, 514/660, 661, 811–813

(56) References Cited

U.S. PATENT DOCUMENTS

| | | | |
|---|---|---|---|
| 4,935,429 | * 6/1990 | Dackis et al. | 514/288 |
| 4,940,585 | 7/1990 | Hapworth et al. | 424/464 |
| 5,189,064 | 2/1993 | Blum et al. | 514/561 |
| 5,217,987 | * 6/1993 | Berger | 514/416 |
| 5,574,052 | 11/1996 | Rose et al. | 514/343 |
| 5,597,832 | 1/1997 | Michaelides et al. | 514/285 |
| 5,824,684 | * 10/1998 | Viner | 514/291 |

OTHER PUBLICATIONS

P. B.S. Clarke, "Nicotinic Receptor Blockade Therapy and Smoking Cessation", *British Journal of Addiction*, 1991, vol. 86, pp. 501–505.

T. Eissenberg et al., "Mecamylamine Does Not Precipitate Withdrawal in Cigarette Smokers", *Psychopharmacology*, 1996, vol. 127, pp. 328–336.

L. H. Ferry, MD, MPH et al., "Efficacy of Bupropion for Smoking Cessation in Non Depressed Smokers", *Journal of Addictive Diseases*, 1994, vol. 13, p. 249.

E. D. Freis, MD et al., "Mecamylamine, a New, Orally Effective, Hypotensive Agent", *Archives of Internal Medicine*, 1956, vol. 97, pp. 551–561.

J. E. Henningfield, Ph.D., "Pharmacologic Basis and Treatment of Cigarette Smoking", *Journal of Clinical Psychiatry*, Dec. 1984, vol. 45:12 (Sec. 2), pp. 24–34.

J. E. Henningfield et al., "Nicotine Medications for Smoking Cessation", *The New England Journal of Medicine*, Nov. 2, 1995, vol. 333, No. 18, pp. 1196–1203.

J. E. Henningfield et al., "Progress in Understanding the Relationship Between the Pharmacological Effects of Nicotine and Human Tobacco Dependence", *Pharmacology Biochemistry & Behavior*, vol. 30, 1988 pp. 217–220.

J. R. Hughes, "Pharmacology for Smoking Cessation: Unvalidated Assumptions, Anomalies, and Suggestions for Future Research", *Journal of Consulting and Clinical Psychology*, 1993, vol. 61, No. 5, pp. 751–760.

J. R. Hughes, Non–Nicotine Pharmacotherapies for Smoking Cessation, *J. Drug Development*, 1994, vol. 6, No. 4, pp. 197–203.

R. D. Hurt, MD et al., "A Comparison of Sustained Release Bupropion and Placebo for Smoking Cessation", *The New England Journal at Medicine*, Oct. 23, 1997, vol. 337, pp. 1195–1202.

M. E. Jarvik et al., "Pharmacological Treatment of Tobacco Dependence", *Pharmacology Biochemistry & Behavior*, 1988, vol. 30, pp. 279–294.

R. M. Keenan, MD et al., "Management of Nicotine Dependence and Withdrawal", in Miller, N.S. (ed.), *Principles of Addiction Medicine*, Chevy Chase, Maryland, American Society of Addiction Medicine, 1994, pp. 1–13.

D. H. Malin et al., "The Nicotinic Antagonist Mecamylamine Precipitates Nicotine Abstinence Syndrome in the Rat", *Psychopharmacology*, 1994, vol. 115, pp. 180–184.

B. R. Martin et al., "What is the Nature of Mecamylamine's Antagonism of the Central Effects of Nicotine?" *Biochemical Pharmacology*, 1989, vol. 38, No. 20, pp. 3391–3397.

P. A. Newhouse et al., "Acute Nicotinic Blockade Produces Cognitive Impairment in Normal Humans", *Psychopharmacology*, 1992, vol. 108, pp. 480–484.

P. A. Newhouse et al., "Age–Related Effects of the Nicotinic Antagonist Mecamylamine on Cognition and Behavior", *Neuropsychopharmacology*, 1994, vol. 10, No. 2, pp. 93–107.

(List continued on next page.)

Primary Examiner—Dwayne C. Jones
Assistant Examiner—C. Delacroix-Muirheid
(74) Attorney, Agent, or Firm—Morgan, Lewis & Bockius LLP

(57) ABSTRACT

The present invention encompasses methods of treating patients for tobacco addiction and nicotine addiction, for palliating the effects of nicotine withdrawal, for providing or facilitating the effects of smoking cessation therapies and as long-term smoking cessation maintenance therapy. The invention also includes related pharmaceutical compositions comprising nicotine receptor antagonists and either an anti-depressant or an anti-anxiety drug. Specific combinations of drugs (mecamylamine HCl and bupropion HCl) as well as mecamylamine in combination with certain drug classes (e.g., anti-anxiety drugs and anti-depressants) comprise the pharmaceutical compositions disclosed. These compositions are also contemplated for use in the treatment of cocaine addiction and the treatment of alcohol dependence.

11 Claims, No Drawings

OTHER PUBLICATIONS

R. Nemeth–Coslett et al., "Effects of Mecamylamine on Human Cigarette Smoking and Subjective Ratings", *Psychopharmacology*, 1986, vol. 88, pp. 420–425.

C. L. Nunn–Thompson et al., "Pharmacotherapy for Smoking Cessation," *Clinical Pharmacy*, Oct. 1989, vol. 8, No. 10, pp. 710–720.

W. B. Pickworth et al., "Mecamylamine Reduces Some EEG Effects of Nicotine Chewing Gum in Humans", *Pharmacology Biochemistry & Behavior*, 1988, vol. 30, pp. 149–153.

W. B. Pickworth et al., "Effects of Mecamylamine on Spontaneous EEG and Performance in Smokers and Non–Smokers", *Pharmacology Biochemistry and Behavior*, 1997, vol. 56, No. 2, pp. 181–187.

C. S. Pomerleau et al., "Mecamylamine Pretreatment Increases Subsequent Nicotine Self–Administration as Indicated by Changes in Plasma Nicotine Level", *Psychopharmacology*, 1987, vol. 91, pp. 391–393.

J. Prignot, "Pharmacological Approach to Smoking Cessation", *Eur. Respir. Journal*, 1989, vol. 2, pp. 550–560.

J. E. Rose, Ph.D., "Nicotine Addiction and Treatment," *Annual Review of Medicine*, 1996, vol. 47, pp. 493–507.

J. E. Rose et al., "Mecamylamine Increases Nicotine Preference and Attenuates Nicotine Discrimination", *Pharmacology Biochemistry & Behavior*, 1989, vol. 32, pp. 933–938.

J. E. Rose, Ph.D. et al., "Mecamylamine Combined with Nicotine Skin Patch Facilitates Smoking Cessation Beyond Nicotine Patch Treatment Alone", *Clinical Pharmacology & Therapeutics*, Jul. 1994, pp. 86–99.

J. E. Rose et al., "Nicotine/Mecamylamine Combination Treatment for Smoking Cessation", *Drug Development Research*, 1996, vol. 38, pp. 243–256.

J. A. Rosecrans et al., "Mecamylamine vs. Nicotine Tolerance", *Journal of Addictive Diseases*, 1994, vol. 13, p. 248.

D. P.L. Sachs, MD et al., "Pharmacologic Approaches to Smoking Cessation", *Clinics in Chest Medicine*, 1991, vol. 12, No. 4, pp. 769–791.

I. P. Stolerman, "Could Nicotine Antagonists be Used in Smoking Cessation?" *British Journal of Addiction*, 1986, vol. 81, pp. 47–53.

I. P. Stolerman et al., "Influencing Cigarette Smoking with Nicotine Antagonists", *Psychopharmacologia (Berl.)*, 1973, vol. 28, pp. 247–259.

F. S. Tennant, Jr. et al., "Clinical Evaluation of Mecamylamine for Withdrawal from Nicotine Dependence", *NIDA Monograph*, 1984, vol. 49, pp. 239–246.

F. S. Tennant, Jr. et al., "Withdrawal from Nicotine Dependence Using Mecamylamine: Comparison of Three–Week and Six–Week Dosage Schedules", *NIDA Monograph*, 1985, vol. 55, pp. 291–297.

D. P. Yells et al., "Monoaminergic Influences on Tmeporal Patterning of Sexual Behavior in Male Rats," *Physiology & Behavior*, 1995, vol 58, No. 5, pp. 847–852.

* cited by examiner

NICOTINE ADDICTION TREATMENT

This application claims priority to U.S. application Ser. No. 60/060,794, filed Oct. 3, 1997, incorporated by reference herein in its entirety.

FIELD OF THE INVENTION

The present invention relates to pharmaceutical compositions and methods of using these compositions to treat patients for tobacco addiction and nicotine addiction, to palliate the effects of nicotine withdrawal and to enhance the outcomes of other smoking cessation therapies. Each agent of the pharmaceutical compositions disclosed has an unique mechanism of action, and when administered concurrently, the combined drugs provide unexpected advantages over existing therapies.

BACKGROUND OF THE INVENTION

Tobacco addiction represents the most important preventable cause of illness and death in our society, responsible for more than 400,000 deaths each year. Currently, one out of five Americans smoke cigarettes, representing almost 50 million smokers in the United States alone. Half of all smokers will die of diseases directly related to tobacco use, and many smokers will suffer significant morbidity. Approximately 15 million smokers try to quit, but only one million of those succeed in smoking cessation each year.

A. Nicotine Addiction and Nicotine Addiction Therapy

A great deal of evidence supports the view that people continue to smoke because of the reinforcing effects of nicotine. Relevant findings include the fact that when allowed to control the nicotine content of each puff, smokers previously deprived of cigarettes, or administered a centrally acting nicotine antagonist, select higher nicotine concentrations. Moreover, under certain conditions, smokers, as well as animals, will self-administer intravenous nicotine.

The rewarding psychopharmacologic effects of nicotine are diverse. They include tranquilization, weight loss, decreased irritability, reduction in craving for cigarettes and other tobacco products, increased alertness, and improved cognitive function. These effects involve to some extent relief of withdrawal symptoms, which could be considered negative reinforcement by nicotine. However, some effects (e.g., improved attentiveness) have been demonstrated in non-dependent animals (Rose, 1996 *Rev. Med.* 47: 493).

Nicotine that is inhaled in tobacco smoke is rapidly absorbed and enters the pulmonary circulation, reaching the brain within several seconds. One cigarette provides 5–30 ng/ml of nicotine in venous blood (Rose, 1996). Nicotine has a metabolic half-life of roughly 2 hours, and cotinine is the main metabolite, Other mechanisms of nicotine delivery, such as snuff, and smoking pipes and cigars create the same effects once in the blood stream.

Nicotine is a powerful psychoactive drug that activates the same brain pathway as cocaine, and other psychostimulants, producing drug associated tolerance and withdrawal effects. In smokers, nicotine's rapid onset of central nervous system action and short half-life cause tolerance to develop quickly and provide an optimal environment for the development of nicotine dependence.

Several pharmacotherapies have proven effective for smoking cessation. These include nicotine replacement therapies (NRTs). Such NRTs come in the form of gum, the transdermal patch, nasal spray, and inhaler. The first FDA-approved pharmaceutical to provide nicotine replacement was Nicorette® (nicotine polacrilex), a chewing gum formulation that contained 2 mg, and later 4 mg, of nicotine in each piece. The gum delivered nicotine through buccal absorption following chewing.

Non-nicotine pharmacologic therapies are a more recently developed method of treating nicotine addiction. Possible reagents include nicotine blockade therapy, drugs affecting serotonergic neurotransmission, anti-depressants, anxiolytics, clonidine and airway sensory replacement (Rose, 1996; and Cinciripini et al., 1998 *Oncology* 12: 249–256). Nicotine blockade therapy (also referred to as nicotine receptor antagonists) utilizes compounds that occupy nicotine receptors, thereby attenuating the reward received from tobacco usage (Clarke, 1991 *Br. J. Addict.* 86: 501–505).

B. Anti-depressants and Anxiolytics

Anti-depressants have oftentimes been used to treat symptoms of nicotine withdrawal. One such anti-depressant is bupropion. Wellbutrin® is the trade name for the bupropion salt, bupropion HCl, an anti-depressant manufactured by Glaxo Wellcome. A sustained-release formulation of bupropion HCl, Wellbutrin SR®, is also indicated for the treatment of depression. Glaxo Wellcome also has FDA approval to market a sustained release formulation of bupropion HCl as an aid to smoking cessation treatment for the smoking cessation indication. Glaxo Wellcome is marketing this product under the trade name Zyban®. Zyban® can be used either alone or in combination with a nicotine transdermal system (NTS). The mechanism of action of bupropion is unknown, but is thought to influence neurotransmitters. Specifically, bupropion is believed to operate on the neurochemistry of nicotine addiction by enhancing dopamine levels in the mesolimbic system and affecting noradrenergic neurons in the locus ceruleus portion of the brain. As dopamine had been associated with the rewarding effects of addictive substances, such as nicotine, inhibition of norepinephrine re-uptake was contemplated to induce a decrease of withdrawal symptoms (*The Medical Letter* 39: 77 (Aug. 15, 1997)).

Another anti-depressant successfully used in the treatment of smoking cessation is doxepin. Doxepin and pharmaceutically acceptable salts thereof were originally administered as anti-depressants (THE MERCK INDEX #3425: 539). Additional anti-depressants considered or utilized for smoking cessation treatment include imipramine (Nunn-Thompson et al., 1989 *Clin. Pharm.* 8: 710–720) and desipramine (Diana et al., 1990 *Am. J. Physiol.* 259: H1718-H1729).

Anxiolytics have also been administered to treat nicotine withdrawal. Anxiolytics counter the mild anxiety symptoms that occur during smoking cessation treatment, or the treatment of alcoholism or other substance abuse. The anxiolytic, isovaleramide, has been recommended for use in smoking cessation (Balandrin et al., WO 94/28888). Smoking cessation has also been treated with a combination of anti-depressants and anxiolytics (Glazer, U.S. Pat. No. 4,788,189)

C. Nicotine Receptor Antagonists

Another class of smoking cessation drugs are nicotine receptor antagonists, which are used to block the nicotinic receptor (Rose et al., 1997 *Psychopharmacology* 130: 28–40). Evidence suggests that smoking cessation may be facilitated by administration of a nicotinic antagonist having a selective action on central nicotinic cholinoceptors of the C6 (ganglionic) type (Clarke, 1987 *Psychopharmacology* 92: 135–143). Additional nicotinic receptors exist against which nicotine antagonists can operate. One nicotine receptor antagonist, mecamylamine and its pharmaceutically acceptable salts, has been explored as a possible pharmacotherapy for smoking cessation because it aids smoking cessation in both animals and humans (Tennant et al., 1984 *NIDA Res. Monogr.* 55: 291–297). Mecamylamine was patented in 1958 and since has been marketed as the anti-hypertensive agent, Inversine®, which is mecamylamine hydrochloride (HCl) (Pfister, U.S. Pat. No. 2,831,027; THE MERCK INDEX #5654: 905). In the context of nicotine dependence, mecamylamine HCl has been shown to block many of the physiologic, behavioral, and reinforcing effects of nicotine.

Low doses of mecamylamine HCl have been shown to enhance smoking cessation when used in combination with a nicotine transdermal system (NTS) (Rose et al., 1994 *Clin. Pharmacology & Therapeutics* 56: 86; Levin et al., U.S. Pat. Nos. 5,574,052 and 5,316,759). In a double-blind clinical trial, in which nicotine was administered by skin patch treatment with or without concurrent mecamylarine (5 mg/bid), a threefold enhancement in continuous smoking abstinence rates was observed for the combined mecamylamine-nicotine patch group compared to the rate observed for the transdermal patch alone. Additionally, the therapeutic effect was sustained for the combined mecamylamine-nicotine patch group, whereas abstinence decreased four fold over 12 months in the NTS-only group. Another effect of the combined mecamylamine-NTS therapy was significantly reduced cravings for cigarettes, negative effect and appetite (Rose et al., 1994).

Thus, because drugs such as mecamylamine, or a pharmaceutically acceptable salt thereof, compete for the same receptor as nicotine, they have been beneficial in enhancing currently available smoking cessation therapies. Mecamylamine is a central and peripheral nicotine antagonist and causes individuals treated with mecamylamine to crave higher doses of nicotine than when the same individual is treated with agents which are peripheral nicotine antagonists only (e.g., trimethaphan) (Perkins et al., "Effects of Central and Peripheral Nicotinic Blockage on Human Nicotine Discrimination," *Psychopharm.* In press). Mecamylamine blocks the stimulus effects of both cytisine and nicotine, both of which bind to neuronal nicotinic receptors (Chandler et al., 1997 *Psychopharmacology* 129: 257–264).

Additional nicotinic antagonists include hexamethonium (Wotring et al., 1995 *Neuroscience* 67: 293–300), dihydro-beta-erythroidine (Stolerman et al., 1997 *Psychopharmacology* 129: 390–397), d-tubocurarine (Wotring et al., 1995), pempidine (Rapier et al., 1990 *J. Neurochem.* 54: 937–945), chlorisondamine (Caggiula et al., 1995 *Psychopharmacology* 122: 301–306), erysodine (Decker et al., 1995 *Eur. J. Pharmacol.* 280: 79–80) and trimethaphan camsylate (Hisayama et al., 1988 *Br. J. Pharmacol.* 95:465–472).

Some nicotinic antagonists have been combined with other agents to examine the effects on mean arterial pressure and renal sympathetic nerve activity. Two nicotinic receptor antagonists, pentolinium and hexamethonium, have been examined in combination with benextramine, desipramine and prazosin for their ability to modulate blood pressure (Martin 1997 *J. Auton. Pharmacol.* 17: 249–259). However, combinations of nicotinic antagonists and either anti-depressants or anxiolytics have not been previously indicated for use in the treatment of smoking cessation or for other substance addiction therapies.

D. Treatment of Cocaine Addiction

Cocaine addiction has been treated with some of the drugs used for smoking cessation as a means of decreasing cocaine withdrawal symptoms. For example pharmacotherapy with desipramine, amantadine and bromocriptine was shown in preliminary studies to minimize the symptoms of cocaine withdrawal (Hall et al., 1990 *Pharmacotherapy* 10: 47–65; and Kosten et al., 1991 *NIDA Res. Monogr.* 105: 510–511).

Combinations of desipramine and amantadine have facilitated greater opiate and cocaine abstinence (Oliveto et al., 1995 *J. Subst. Abuse Treat.* 12: 423–428).

SUMMARY OF THE INVENTION

The present invention relates to a pharmaceutical composition for treating tobacco addiction and nicotine addiction, for palliating nicotine withdrawal symptoms or facilitating smoking cessation. The preferred compositions comprise a therapeutically effective combination of a nicotine receptor antagonist and either an anti-depressant or an anti-anxiety drug absent supplementation of nicotine. Contemplated pharmaceutical compositions can be an admixture of the active agents administered as a single unit (e.g., a single tablet or capsule) or can be administered in separate dosage units (e.g., two capsules).

The anti-depressant of the pharmaceutical composition contemplated for this invention can be bupropion or a pharmaceutically acceptable salt thereof, or doxepin or a pharmaceutically acceptable salt thereof. Additional anti-depressants contemplated for combination with a nicotinic antagonist include: doxepin, desipramine, clomipramine, imipramine, nortriptyline, amitriptyline, protriptyline, trimipramine, fluoxetine, fluvoxamine, paroxetine, sertraline, phenelzine, tranylcypromine, amoxapine, maprotiline, trazodone, venlafaxine, mirtazapine, their pharmaceutically active salts or their optical isomers.

One pharmaceutically acceptable salt of bupropion contemplated for the invention to be used in combination with a nicotine receptor antagonist is bupropion hydrochloride (HCl). The amount of bupropion or its pharmaceutically acceptable salt to be administered with a nicotine receptor antagonist is formulated so as to provide a dose of about 50 mg to about 300 mg per day.

One pharmaceutically acceptable salt of doxepin contemplated for the invention to be used in conjunction with a nicotine receptor antagonist is doxepin hydrochloride (HCl). It is further contemplated that the amount of doxepin or pharmaceutically acceptable salt thereof to be administered with a nicotine receptor antagonist is formulated so as to provide a dose of about 10 mg to a dose of about 300 mg of doxepin per day. The total daily dose can be administered in several dosages over the course of the day (e.g., 1 to 6 tablets).

It is also contemplated that the nicotine receptor antagonist component of the pharmaceutical composition is mecamylamine and pharmaceutically acceptable salts thereof as well as optical isomers. One pharmaceutically acceptable salt of mecamylamine disclosed herein is mecamylamine hydrochloride (HCl). It is further contemplated that the amount of mecamylamine, or pharmaceutically acceptable salt thereof, to be administered with either an anti-depressant or an anti-anxiety drug is formulated to provide a dose of about 1 mg to about 25 mg of mecamylamine per day.

The invention further relates to the use of the anti-anxiety drug, buspirone or pharmaceutically acceptable salts thereof in combination with a nicotine receptor antagonist. It is contemplated that buspirone hydrochloride (HCl) in combination with a nicotine receptor antagonist be utilized. The invention also relates to the use of an amount of buspirone or pharmaceutically acceptable salt thereof to be administered with a nicotine receptor antagonist that is formulated so as to provide a dose of about 5 mg to a dose of about 60 mg per day. More preferred is the use of a nicotine receptor antagonist in a dosage range of about 1 mg to about 25 mg of mecamylamine (HCl) to be administered in conjunction with a dosage of buspirone (HCl) of about 5 mg to about 10 mg per tablet. These dosages may be administered as one tablet to six tablets per day. Anxiolytics other than buspirone contemplated for coadministration with a nicotinic antagonist for the treatment of smoking cessation include: hydroxyzine or meprobamate.

This invention further provides compositions containing nicotinic antagonists, other than mecamylamine, and either an anxiolytic or an anti-depressant. The nicotinic antagonists include: central nicotinic antagonists, central and peripheral nicotinic antagonists and peripheral nicotinic antagonists. Specific nicotinic antagonists contemplated include: mecamylamine, amantadine, pempidine, dihydro-beta-erythroidine, hexamethonium, erysodine, chlorisondamine, trimethaphan camsylate, tubocurarine chloride, d-tubocurarine, their pharmaceutically acceptable salts or their optical isomers.

The invention additionally relates to a method of treating tobacco addiction or nicotine addiction, palliating nicotine withdrawal symptoms, or facilitating smoking cessation comprising the step of administering to a patient any one of the aforementioned pharmaceutical compositions.

The invention farther relates to a method of treating tobacco addiction or nicotine addiction, palliating nicotine withdrawal symptoms, or facilitating smoking cessation comprising the added step of administering the pharmaceutical compositions disclosed above in combination with a nicotine replacement or supplementation therapy. The nicotine transdermal patch is such a contemplated nicotine replacement therapy.

It is further contemplated that the described pharmaceutical compositions can be administered to treat individuals for cocaine addiction, to ameliorate cocaine withdrawal symptoms and to treat individuals for alcohol addiction and ameliorate the effects associated with alcohol withdrawal. The methods of delivery and dosages administered for treatment of cocaine addiction and alcohol dependence may be similar to those suggested for treatment of nicotine addiction.

DETAILED DESCRIPTION OF THE PREFERRED EMBODIMENT

I. General Description

Although non-prescription nicotine replacement therapies dominate the market, their effectiveness in preventing nicotine-dependent individuals from relapsing is not as great as that demonstrated for non-nicotine dependent pharmacological agents, such as bupropion HCl. Success rates for nicotine gum is less than 10% at 12 months and for nicotine transdermal patches only 10–30% at 12 months (Rose et al., 1994). Therefore, identifying reagents that possess low failure rates are a goal for both the industry and for smokers desiring to quit their addictive habit.

The present invention encompasses methods of treating patients for tobacco addiction, nicotine addiction, palliating the effects of nicotine withdrawal, enhancing the outcomes of other smoking cessation therapies, as well as providing long term smoking cessation maintenance treatment. The invention also includes related pharmaceutical compositions used to treat patients administered in therapeutically effective amounts. Specific combinations of drugs, such as an anti-anxiety agent in combination with a nicotine receptor antagonist are disclosed. Additionally, the pharmaceutical composition of an anti-depressant in combination with a nicotine receptor antagonist is also contemplated. Preferred nicotinic receptor antagonists are those that are both a central and peripheral nicotine antagonist (e.g., mecamylamine) or a central nicotinic agonist. Less preferred nicotinic receptor antagonists are those antagonists which are only peripheral nicotine antagonists. These compositions are also contemplated for use in treating individuals for cocaine addiction and its associated withdrawal effects, and alcohol dependence and its associated withdrawal effects.

II. Specific Description

In one embodiment, the pharmaceutical compositions of this invention that are used to treat tobacco addiction and palliate the withdrawal symptoms associated with cessation of tobacco use, preferably include the following combinations:

(1) mecamylamine or a pharmaceutically acceptable mecamylamine salt such as mecamylamine hydrochloride (HCl) and bupropion or a pharmaceutically acceptable bupropion salt, such as bupropion hydrochloride (HCl);

(2) mecamylamine or a pharmaceutically acceptable mecamylamine salt, such as mecamylamine HCl and buspirone or a pharmaceutically acceptable buspirone salt, such as buspirone hydrochloride (HCl);

(3) mecamylamine or a pharmaceutically acceptable mecamylamine salt such as mecamylamine HCl and doxepin or a pharmaceutically acceptable doxepin salt, such as doxepin hydrochloride (HCl); and (4) a nicotine receptor antagonist and either an anti-depressant or an anti-anxiety agent.

The patents that exist for the anti-depressants, anti-anxiety drugs (also known as anxiolytics), and nicotine antagonists, such as mecamylamine, identified below discuss other uses for these agents. These patents describe the pharmaceutical compositions and their pharmaceutically acceptable salt derivatives, methods of producing the pharmaceuticals and methods of using them.

Although large dosage ranges are contemplated for the nicotine receptor antagonist-anti-depressant and nicotine receptor antagonist-anxiolytic combinations, due to the unexpected advantages created by the combination therapy, preferred dosages may lie in the low to mid range for each drug. These lower dosages will reduce the incidence of side effects and adverse reactions.

Mecamylamine was used initially as an anti-hypertensive, but also can act as a nicotine receptor antagonist. U.S. Pat. No. 2,831,027 describes the synthesis of mecamylamine. The mecamylamine salt, mecamylamine HCl, has the chemical formula of $C_{11}H_{22}ClN$. Mecamylamine and pharmaceutically or physiologically acceptable salts thereof (e.g., mecamylamine HCl) and optical isomers are contemplated in this invention to be used in combination with an anti-anxiety drug or an anti-depressant to treat tobacco addiction and nicotine addiction, ameliorate nicotine withdrawal effects, in conjunction with nicotine replacement therapies (NRTs), and to treat cocaine addiction and alcohol dependence.

Nicotinic antagonists, in addition to mecamylamine, contemplated for use in combination with an anxiolytic or an anti-depressant include dihydro-beta-erythroidine (also known as dihydro-β-erythroidine; 3β-1,6-didehydro-14,17-dihydro-3-methoxy-16(15H)-oxaerythrinan-15-one; 12,13-didehydro-2,7,13, 14 tetrahydro-α-erythroidine) (THE MERCK INDEX, #3158: 500;1989); tubocurarine chloride (also known as 7',12'-dihydroxy-6,6-dimethoxy-2,2',2'-trimethyltubocuraranium chloride hydrochloride) (THE MERCK INDEX, #9717: 1542, 1989); d-tubocurarine (Wotring et al., 1995); amantadine (also known as tricyclo [3.3.1.1$^{3,7}$]decan-1-amine; 1-adamantanamine; 1-aminoadamantane; 1-aminodiamantane; 1-aminotricyclo [3.3.1.1$^{3,7}$]decane) (THE MERCK INDEX #380: 60, 1989); pempidine (also known as 1,2,2,6,6-pentamethylpiperidine) (THE MERCK INDEX #7022: 1120, 1989); erysodine (an erythrine alkaloid related to dihydro-beta-erythroidine; see Decker et at., 1995; and Singh et al., 1969 *Experientia* 25: 785); chlorisondamine (also known as chlorisdondamine chloride; 4,5,6,7-tetrachloro-2,3-dihydro-2-methyl-2-[trimethylammonio)ethyl]-2H-isoindolium dichloride; 4,5, 6,7-tetrachloro-2-(2-dimethylaminoethyl)-2-methylisoindolinium chloride methochloride) (THE MERCK INDEX #2101: 324–325, 1989); hexamethonium (also known as N,N,N,N',N',N'-hexamethyl-1,6-hexanediaminium; hexmethylenebis(trimethylammonium) (THE MERCK INDEX #4609: 741, 1989); and trimethaphan camsylate (also known as decahydro-2-oxo-1, 3bis (phenylmethyl)thienol[1',2':1,2]thieno[3,4]imidazol-5-ium (THE MERCK INDEX #962 1: 1527, 1989). The pharmaceutical salts of these compounds are also contemplated for use in the treatment of smoking cessation. One example using a nicotinic antagonist other than mecamylamine is amantadine HCl and bupropion, wherein about 150 mg to about 300 mg of bupropion is co-administered with about 50 mg to about 150 mg of amantadine HCl to treat smoking cessation, as well as other conditions involving withdrawal symptoms.

This invention also relates to use of an anti-depressant, such as bupropion, in conjunction with a nicotine receptor antagonist. U.S. Pat. Nos. 3,819,706 and 3,885,046 describe the synthesis of bupropion. The various forms of bupropion have been used to treat psychosexual dysfunction in men and women, to reduce cholesterol levels, to treat attention deficit disorder (ADD), to suppress prolactin levels in animals, to treat depression, to treat tardive dyskinesia in mammals, and to overcome the mental alertness impairments created by alcohol consumption. Patents encompassing the aforementioned methods of using bupropion are disclosed respectively in U.S. Pat. Nos. 4,507,323; 4,438, 138; 4,435,449; 4,347,257; 3,885,046; 4,425,363; and 4,393,078. One pharmaceutically acceptable salt of bupropion, bupropion HCl, which is marketed under the names of Wellbatrin® and Wellbutrin®, has the chemical formula of $C_{11}H_{19}Cl_2NO$.

Another anti-depressant contemplated for administration with a nicotine receptor antagonist is doxepin or pharmaceutically acceptable salts thereof. U.S. Pat. Nos. 3,438,981 and 3,420,851 describe the synthesis, pharmaceutical composition and use of doxepin. Doxepin has the chemical formula of $C_{19}H_{21}NO$. One pharmaceutically acceptable salt of doxepin, doxepin HCl, has the chemical formula of $C_{19}H_{22}ClNO$ and is marketed under the names Adapin®, Aponal®, Curatin®, Novoxapin®, Quitaxon® and Sinequan®. Doxepin and pharmaceutically or physiologically acceptable salts have been administered as anti-depressants or anti-pruritics (THE MERCK INDEX, #3425: 539). As contemplated for use in this invention, doxepin is to be administered with a nicotine receptor antagonist to treat the effects of tobacco addiction and nicotine addiction, to palliate nicotine withdrawal effects, and to potentiate other smoking cessation therapies. These pharmaceutical compositions may also be used to treat cocaine addiction or to treat alcohol dependence.

Additional anti-depressants contemplated for administration with nicotine receptor antagonists include: amitriptyline (100–30 mg per day), clomipramine (200–250 mg per day), desipramine (100–300 mg per day), imipramine (100–300 mg per day), nortriptyline (50–200 mg per day), protriptyline (20–60 mg per day), trimipramine (100–300 mg per day), fluoxetine (10–80 mg per day), fluvoxamine (100–300 mg per day), paroxetine (20–50 mg per day), sertraline (50–200 mg per day), phenelzine (45–90 mg per day), tranylcypromine (20–50 mg per day), amoxapine (200–600 mg per day), maprotiline (150–200 mg per day), trazodone (200–600 mg per day), nefazodone (300–600 mg per day), venlafaxine (75–375 mg per day), and mirtazapine (15–45 mg per day); and their pharmaceutically acceptable salts and optical isomers. The preferred dosage ranges for the pharmaceutical composition comprising a nicotine receptor antagonist and one of the above listed anti-depressants would likely lie in the low to mid-range dosages suggested for each agent.

In addition to anti-depressants, anxiolytics can be administered with nicotine receptor antagonists either in admixture or administered separately. One anxiolytic agent contemplated is buspirone and pharmaceutically acceptable salts thereof, such as buspirone HCl. U.S. Pat. Nos. 3,717,634 and 4,182,763 describe the synthesis, pharmaceutical composition and use of buspirone as an anxiolytic. Buspirone has its the chemical formula of $C_{21}H_{31}N_5O_2$. Its synthesis is described in U.S. Pat. No. 3,717,634. Buspirone and its pharmaceutically acceptable salts, such as buspirone HCl, are useful as nonbenzodiazepine anxiolytics and as 5-hydroxytryptamine (5-HT$_1$) receptor agonists (THE MERCK INDEX, #1493: 539). Buspirone HCl has the chemical formula of $C_{21}H_{32}ClN_5O_2$ and commercially is marketed under such names as Bespar®, Buspare®, Buspinol®, Censpar®, Lucelan® and Travine®.

Other non-benzodiazepine anxiolytics are also contemplated for use in conjunction with a nicotine receptor antagonist to treat smoking cessation. Additional anxiolytics include: hydroxyzine (50–400 mg per day) and meprobamate (400–1600 mg per day). The preferred dosage range for such drug combinations may lie in the low to mid-range of the suggested ranges due to simultaneous administration with a nicotinic antagonist. In turn, these lower dosages reduce the risk of adverse side effects.

A preferred embodiment of the invention is the pharmaceutical composition comprising a dose formulated to deliver about 1 mg mecamylamine HCl to about 25 mg mecamylamine HCl per day and from about 50 mg bupropion HCl to about 300 mg bupropion HCl per day. A more preferred embodiment would be a pharmaceutical composition comprising a dose formulated to deliver about 1 mg mecamylamine HCl to about 10 mg mecamnylamine HCl per day and a dose formulated to deliver about 50 mg bupropion HCl to about 300 mg bupropion HCl. The most preferred embodiment comprises a dose formulated to deliver about 1 mg mecamylamine HCl to about 5 mg mecamylamine HCl per day and from about 50 mg bupropion HCl to about 300 mg bupropion HCl per day. These formulations could be administered either in one pill once a day or via several pills, up to about 6 formulated units (e.g., tablets or capsules) per day. The maximum recommended daily dose suggested for mecamylamine HCl and bupropion HCl are generally 25 mg and 300 mg respectively. Alternatively, another contemplated embodiment is a formulated pharmaceutical composition that releases the active ingredients over time. Such pharmaceutical compositions are also contemplated for use in treating cocaine addiction and withdrawal symptoms associated with cocaine addiction, and alcohol dependence and its associated withdrawal effects.

Another preferred embodiment is the pharmaceutical composition of buspirone HCl (Buspar®, Mead Johnson) in combination with mecamylamine HCl to be used to treat tobacco addiction, nicotine addiction, to palliate the side effects of nicotine withdrawal, to improve long term withdrawal from smoking, or to enhance nicotine replacement therapies.

The pharmaceutical composition preferably comprises a dose of buspirone HCl of about 5 mg to about 10 mg per day and a dose of mecamylamine HCl of about 1 mg to about 25 mg per day. These formulations could be administered either in one pill once a day or via several pills, up to about 6 formulated units (e.g., tablets or capsules) per day; the maximum recommended daily dosages of buspirone HCl and mecamylamine HCl are generally 60 mg and 25 mg respectively. Another contemplated embodiment is a formulated time release pharmaceutical composition that releases the active ingredients over time. This would include formulations comprising a buspirone HCl dose of about 5 mg per day and a dose of about 25 mg per day of mecamylamine HCl, as well as a dose of buspirone HCl of about 10 mg per day and a dose of about 1 mg per day of mecamylamine HCl. Other possible combinations will be apparent to an individual schooled in the art in light of the dosage range suggested herein. These formulations are also considered for treating withdrawal effects related to cocaine addiction, and alcohol dependence and its associated withdrawal effects.

Another preferred embodiment using a nicotine receptor antagonist in conjunction with an anti-depressant is the pharmaceutical composition of doxepin HCl in combination with mecamylamine HCl. Contemplated pharmaceutical compositions comprise a dose of doxepin HCl of about 10 mg to about 300 mg per day and a dose of mecamylamine HCl of about 1 mg to about 25 mg per day administered either separately (e.g., each drug is dispensed in separate capsules or tablets) or in one unit, such as one capsule or tablet. These formulations could be administered either in one pill once a day or via several pills, up to 6 formulated units (e.g., tablets or capsules) per day. A more preferred formulation would comprise a dose of about 10 mg to about 150 mg per day of doxepin and a dose of mecamylamine HCl of about 1 mg to about 25 mg per day. The most preferred formulation would comprise a dosage of 5 mg mecamylamine HCl and a dosage of about 75 mg of doxepin HCl administered twice daily (e.g., morning and evening). Alternatively, another contemplated embodiment is a formulated time release pharmaceutical composition that would deliver the active ingredients over time. This would include formulations comprising a doxepin HCl dose of about 50 mg per day and a dose of about 25 mg per day of mecamylamine HCl. Other possible combinations will be apparent to an individual schooled in the art in light of the dosage range suggested herein. The recommended maximum daily dose for mecamylamine HCl and doxepin HCl are generally 25 mg and 300 mg respectively. Such pharmaceutical compositions are also contemplated for use in treating cocaine addiction and withdrawal effects associated with cocaine addiction, and alcohol dependence and its associated withdrawal effects.

The contemplated combinations of pharmaceutical compositions discussed above can be prepared for oral, parenteral, rectal or buccal administration, or in a form suitable for administration by inhalation or insufflation to the average adult human for treatment of tobacco addiction and nicotine addiction, to treat the effects of nicotine and tobacco withdrawal, to improve long term abstinence from smoking, or to enhance smoking cessation therapies (e.g., nicotine replacement therapies, such as the nicotine transdermal patch or Nicorette® gum). The pharmaceutical compositions may further be formulated using one or more pharmaceutically acceptable carriers and excipients. The drugs can be administered in a single unit (e.g., one tablet) or as two or more separate drugs.

For oral administration, the pharmaceutical compositions disclosed may take the form of, for example, tablets or capsules prepared by conventional means in admixture with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate); glidants; artificial and natural flavors and sweeteners; artificial or natural colors and dyes; and solubilizers. The pharmaceutical compositions may be additionally formulated to release the active agents in a time-release manner as is known in the art and as discussed in U.S. Pat. Nos. 4,690,825 and 5,055,300. The tablets may be coated by methods well known in the art.

Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

For buccal administration, the composition may take the form of tablets or lozenges formulated in conventional manners.

The active compounds may be formulated for parenteral administration by injection, which include using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredients may be in powder form for reconstitution with a suitable vehicle, e.g., sterile pyrogen-free water, before use.

The active compounds may also be formulated in rectal compositions such as suppositories or retention enemas, e.g., containing conventional suppository bases such as cocoa butter or other glycerides.

For intranasal administration or administration by inhalation, the active compounds are conveniently delivered in the form of a solution or suspension from a pump spray container that is squeezed or pumped by the patient, or as an aerosol spray presentation from a pressurized container or nebulizer, with the use of a suitable propellant (e.g., dichlorodifluoromethane, trichlorofluoromethane, dichlorotetrafluoroethane, carbon dioxide or other suitable gas). In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of an active compound and a suitable powder base such as lactose or starch.

Without further description, it is believed that one of ordinary skill in the art, using the preceding description and the following illustrative examples, can make and utilize the compounds of the present invention and practice the claimed methods. Additionally, all of the preceding pharmaceutical compositions comprising a nicotine receptor antagonist and either an anti-depressant or an anti-anxiety drug to treat nicotine dependence and smoking cessation can be used in conjunction with a nicotine replacement therapy (e.g., nicotine transdermal patch). These compositions and methods of administration are also contemplated for use in treating both cocaine addiction and alcohol dependence. The following working examples therefore, specifically point out preferred embodiments of the present invention, and are not to be construed as limiting in any way the remainder of the disclosure. Other generic configurations will be apparent to one skilled in the art.

EXAMPLES

Example 1

A formulation comprising about 1.0 mg mecamylamine and about 50 mg bupropion is combined into a single tablet or capsule and is administered orally at a dose frequency between one to six tablets daily.

Example 2

A formulation comprising about 1.0 mg mecamylamine and about 150 mg bupropion is combined into a single tablet or capsule and is administered orally at a dose frequency between one to six tablets daily.

Example 3

A formulation comprising about 5 mg mecamylamine and about 50 mg bupropion is combined into a single tablet or capsule and is administered orally at a dose frequency between one to six tablets daily.

Example 4

A formulation comprising about 5 mg mecamylamine and about 150 mg bupropion is combined into a single tablet or capsule and is administered orally at a dose frequency between one to six tablets daily.

Example 5

A formulation comprising about 25 mg mecamylamine and about 300 mg bupropion is combined into a single tablet or capsule and is administered orally in one dose. This dosage is also contemplated to be administered in a pharmaceutical composition that releases the active ingredients over time (e.g., 24 hours).

Example 6

A 2.5 mg tablet of mecamylamine is taken orally three times daily, and a 150 mg tablet of bupropion is taken twice daily, in the morning and evening.

Example 7

Use of mecamylamine with other anti-depressants

Other anti-depressants, such as but not limited to doxepin HCl (Sinequan®, Pfizer), may also be used in combination with mecamylamine. Doxepin HCl in a dose range between about 10 mg and about 150 mg is administered in combination with mecamylamine HCl in a dose range between about 1 mg and about 25 mg. These dosages can be administered in several smaller unit formulations over the course of day (e.g., 1 to 6 capsules).

Example 8

Use of mecamylamine with anti-anxiety agents

The anxiolytic, buspirone HCl (Buspar®, Mead Johnson), a 5-hydroxytryptamine (5-$HT_1$) agonist, has also demonstrated effectiveness in combating nicotine-related withdrawal symptoms and increasing short-term smoking abstinence. This agent, as well as other antianxiety drugs, may also be utilized in combination with mecamylamine HCl to improve long term withdrawal from smoking. Buspirone HCl in a dose of about 5 mg to about 10 mg is used in combination with mecamylamine HCl in a dose of about 1 mg to about 25 mg. This would include a buspirone HCl dose of about 5 mg with approximately 25 mg of mecamylamine HCl, as well as a dose of buspirone HCl of about 10 mg and a dose of about 1 mg mecamylamine HCl. These dosages would likely be administered twice daily, ie., morning and evening, but can be administered more or less frequently as needed. Other possible combinations will be apparent to an individual schooled in the art in light of the dosage range suggested herein.

REFERENCES

This application also incorporates in its entirety, the U.S. Provisional Application No. 60/060,794 filed Oct. 3, 1997. The following references and all articles, texts and patents referred to above and below, are hereby incorporated by reference in their entirety:

A. W. Peck, U.S. Pat. No. 4,393,078 (1983)
B. M. Bloom et al., U.S. Pat. No. 3,420,851 (1969)
Balandrin et al., WO 94/28888
Bupropion HCl, THE MERCK INDEX Eleventh Edition #1488 (1989): 228
Bupropion (Zyban®) for Smoking Cessation, *The Medical Letter* 39(1007): 77 (Aug. 15, Buspirone, THE MERCK INDEX Eleventh Edition #1493 (1989): 229
Caggiula et al., 1995 *Psychopharmacology* 122: 301–306
Casten et al., U.S. Pat. No. 4,182,763 (1980)
Chandler et al., 1997 *Psychopharmacology* 129: 257–264
Cinciripini et al., 1998 *Oncology* 12: 249–256
Clarke, 1991 *Br. J. Addict.* 86: 501–505
Clarke, 1987 *Psychopharmacology* 92: 135–143
Decker et al., 1995 *Eur. J. Pharmacol.* 280: 79–89
Diana et al., 1990 *Am. J. Physiol.* 259: H1718-H1729)
Doxepin, THE MERCK INDEX Eleventh Edition #3425 (1989): 539
Glazer, U.S. Pat. No. 4,788,189
Gupta, U.S. Pat. No. 5,055,300 (1991)
Hall et al., 1990 *Pharmacotherapy* 10: 47–65
Hisayama et al., 1988 *Br. J. Pharmacol.* 95: 465–472
Kosten et al., 1991 *NIDA Res. Monogr.* 105: 510–511
Martin 1997 *J. Auton. Pharmacol.* 17: 249–259
Mecamylamine HCl, THE MERCK INDEX Eleventh Edition #5654 (1989): 905
Mehta, U.S. Pat. No. 3,819,706 (1974)
Mehta, U.S. Pat. No. 3,885,046 (1975)
THE MERCK INDEX #380: 60 (1989)
THE MERCK INDEX #2101: 324–325 (1989)
THE MERCK INDEX #3158: 500 (1989)
THE MERCK INDEX #4609: 741 (1989)
THE MERCK INDEX #7022: 1120 (1989)
THE MERCK INDEX #9621: 1527 (1989)
THE MERCK INDEX, #9717: 1542 (1989)

Nunn-Thompson et al., 1989 *Clin. Pharm.* 8: 710–720
Oliveto et al., 1995 *J. Subst. Abuse Treat.* 12: 423428
Perkins et al., "Effects of Central and Peripheral Nicotinic Blockage on Human Nicotine Discrimination," *Psychopharm.* In press
Pfister, U.S. Pat. No. 2,831,027 (1958)
Rapier et al., 1990 *J. Neurochem.* 54: 937–945
Rose, "nicotine addiction and treatment," 1996 *Annu. Rev. Med.* 47: 493
Rose et al., "Mecamylamine combined with nicotine skin patch facilitates smoking cessation beyond nicotine patch treatment alone," 1994 *Clin. Pharmacology & Therapeutics.* 56: 86–99 (1994)
Rose et al., 1997 *Psychopharmacology* 130: 28–40
Singh et al., 1969 *Experientia* 25: 785
Stach, U.S. Pat. No. 3,438,981 (1969)
Stern, U.S. Pat. No. 4,507,323 (1985)
Stern, U.S. Pat. No. 4,425,363 (1984)
Stern, U.S. Pat. No. 4,435,449 (1984)
Stern, U.S. Pat. No. 4,438,138 (1984)
Stern, U.S. Pat. No. 4,347,257 (1982)
Stolerman et al., 1997 *Psychopharmacology* 129: 390–397
Tennant et al., 1984 *NIDA Res. Monogr.* 55: 291–297
Won, U.S. Pat. No. 4,690,825 (1987)
Wotring et al., 1995 *Neuroscience* 67: 293–300
Wu et al., U.S. Pat. No. 3,717,634 (1973)

What is claimed is:

1. A pharmaceutical composition for treating tobacco addiction or nicotine addiction, palliating nicotine withdrawal symptoms or facilitating smoking cessation comprising a therapeutically effective combination of mecamylamine, a pharmaceutically acceptable salt thereof or an optical isomer thereof and bupropion, a pharmaceutically acceptable salt thereof, or an optical isomer thereof, wherein the bupropion is formulated to deliver a daily dose of about 50 mg to about 250 mg.

2. The pharmaceutical composition of claim 1, wherein said pharmaceutically acceptable salt of bupropion is bupropion HCl.

3. The pharmaceutical composition of claim 1, wherein said pharmaceutically acceptable salt of mecamylamine is mecamylamine HCl.

4. The pharmaceutical composition of claim 1, wherein said bupropion or a pharmaceutically acceptable salt thereof is formulated to deliver a daily dose of about 50 mg to about 200 mg.

5. The pharmaceutical composition of claim 1, wherein said bupropion or a pharmaceutically acceptable salt thereof is formulated to deliver a daily dose of about 50 mg to about 150 mg.

6. The pharmaceutical composition of claim 1, wherein said mecamylamine or a pharmaceutically acceptable salt thereof is formulated to deliver a daily dose of about 1 mg to about 25 mg.

7. The pharmaceutical composition of claim 6, wherein said mecamylamine or a pharmaceutically acceptable salt thereof is formulated to deliver a daily dose of about 1 mg to about 10 mg.

8. A method of treating tobacco addiction or nicotine addiction, palliating nicotine withdrawal symptoms or facilitating smoking cessation comprising the step of administering to a patient the pharmaceutical composition of claim 1.

9. The method of claim 8, comprising the further step of administering nicotine replacement therapy.

10. The method of claim 9, wherein said nicotine replacement therapy is a nicotine transdermal patch.

11. The method of claim 8, wherein the composition is administered orally, parenterally, rectally, bucally, or by inhalation or insufflation.

* * * * *